(12) United States Patent
Lo et al.

(10) Patent No.: US 9,441,003 B2
(45) Date of Patent: Sep. 13, 2016

(54) MEMBRANE STAINING DYES CONTAINING PHOSPHORESCENT TRANSITION METAL POLYPYRIDINE COMPLEXES

(71) Applicant: City University of Hong Kong, Kowloon (HK)

(72) Inventors: Kam-Wing Kenneth Lo, Hong Kong (HK); Yin Zhang, Nanjing (CN); Tsan-Shing Lau, Hong Kong (HK); Lijuan Hua, Hong Kong (HK)

(73) Assignee: CITY UNIVERSITY OF HONG KONG, Hong Kong (HK)

( * ) Notice: Subject to any disclaimer, the term of this patent is extended or adjusted under 35 U.S.C. 154(b) by 38 days.

(21) Appl. No.: 14/250,527

(22) Filed: Apr. 11, 2014

(65) Prior Publication Data

US 2015/0293108 A1 Oct. 15, 2015

(51) Int. Cl.
*C07F 15/00* (2006.01)
*G01N 1/30* (2006.01)

(52) U.S. Cl.
CPC ............. *C07F 15/0033* (2013.01); *G01N 1/30* (2013.01)

(58) Field of Classification Search
CPC ............................. C07F 15/0033; G01N 1/30
USPC .................................................. 546/4; 435/29
See application file for complete search history.

(56) References Cited

PUBLICATIONS

Frida R. Svensson et al., Lipophilic Ruthenium Complexes with Tuned Cell Membrane Affinity and Photoactivated Uptake, Biophysical Chemistry 149 (2010) pp. 102-106.
Chi-Kin Koo et al., Two-Photon Plasma Membrane Imaging in Live Cells by an Amphiphilic, Water-Soluble Cyctometalated Platinum (II) Complex, Inorganic Chemistry, 48 (2009) pp. 7501-7503.

*Primary Examiner* — Porfirio Nazario Gonzalez
(74) *Attorney, Agent, or Firm* — Heslin Rothenberg Farley & Mesiti P.C.; Melvin S. Li, Esq.

(57) ABSTRACT

The present invention is concerned with a staining dye for staining a biological cell, comprising dye molecules with a positively charged polar head group for attraction to cell membrane of the cell and for refraining the dye molecules from entering the cytoplasm, and one or more hydrophobic groups for interaction with phospholipids of the cell membrane. The dye molecules are phosphorescent transition metal polypyridine complexes having a metal center and ligands which are non-organic fluorophores.

5 Claims, 8 Drawing Sheets
(3 of 8 Drawing Sheet(s) Filed in Color)

Synthetic route of the ligands bpy-R:

Fig. 9

Synthetic route of the complexes [Ir(ppyCH₂NH-C10)₂(bpy-R)]Cl:

Fig. 10

MEMBRANE STAINING DYES CONTAINING PHOSPHORESCENT TRANSITION METAL POLYPYRIDINE COMPLEXES

FIELD OF THE INVENTION

The present invention is concerned with membrane staining dyes containing dye molecules having phosphorescent transition metal polypyridine complexes, and methods of making thereof.

BACKGROUND OF THE INVENTION

Membrane staining dyes for biological cells are important reagents for cell surface demarcation and for investigation of different cellular processes. The staining pattern of individual cells can mark cellular and thus illustrate functions such as endocytosis and exocytosis. In multicellular organisms, membrane dyes are useful for tracking cell migration, transplantation, adhesion, and fusion. Such tracking can be very useful in studying, for example, cell developmental biology of the organisms, leading to new diagnostics and therapeutic means. Accordingly, such dyes can be useful tools in carrying out such studies. Compared with other organelle-specific stains, membrane dyes are relatively rare because most compounds, for example, either undergo internalization efficiently or are membrane-impermeable, rendering them unsuitable or deficient in serving as biological cell membrane dyes.

The present invention is concerned with improved membrane staining dyes and methods of making thereof, or at least to provide useful alternatives to the public.

SUMMARY OF THE INVENTION

According to a first aspect of the present invention, there is provided a staining dye for staining a biological cell, comprising dye molecules with a positively charged polar head group for attraction to cell membrane of the cell, and one or more hydrophobic groups for interaction with phospholipids of the cell membrane and for minimizing the dye molecules from entering the cell, wherein the dye molecules are transition metal polypyridine complexes having a metal center and ligands which are non-organic fluorophores.

Preferably, the hydrophobic group may have one or more hydrophobic tails.

Suitably, the complexes may have non-polar moieties for interaction with lipid bilayer of the cell membrane and polar groups for refraining the complexes from entering the cytoplasm rapidly.

In an embodiment, the metal center may be selected from a group containing iridium(III), rhenium(I) and ruthenium (II).

In one embodiment, the chemical formula and the structural formula of the dye molecules may be:

respectively, wherein n≥4; R is a variable substituent.

In a specific embodiment, the chemical formula and the structural formula of the dye molecule may be:

respectively.

In another specific embodiment, the chemical formula and the structural formula of the dye molecule may be:

[Ir(ppyCH₂NH—C10)₂(bpy)—COOH]Cl and respectively.

In yet another specific embodiment, the chemical formula and the structural formula of the dye molecule may be:

[Ir(ppyCH₂NH—C10)₂(bpy)—Me)]Cl and respectively.

According to a second aspect of the present invention, there is provided a processed biological cell, stained with a dye as described.

According to a third aspect of the present invention, there is provided a method of synthesizing a dye as described above, comprising steps of synthesizing the ligands bpy-R of, said steps including:
  subjecting 4,4'-dimethyl-2,2'-bipyridine to first oxidation for forming an aldehyde;
  subjecting said aldehyde to second oxidation for forming 4-carboxy-4'-methyl-2,2'-bipyridine (bpy-COOH); and
  subjecting said aldehyde to reductive animation for forming the ligands bpy-R.

Preferably, the first oxidation may be performed in the presence of selenium oxide. The second oxidation may be performed in the presence of silver oxide (generated in situ by reaction of silver nitrate and sodium hydroxide). Alternative reductive amination may be performed in the presence of NaBH₄. The following diagram illustrates specific example for synthesizing the dye as described above.

-continued

The method may comprise steps of synthesizing complexes [Ir(ppyCH₂NH—C10)₂(bpy-R)]Cl under reflux for 24 h in the dark in an nitrogen atmosphere:

reacting iridium(III) chloride salt with 4-(2-pyridyl)benzaldehyde forming orange dimer;

subjecting the orange dimer to reductive amination with n-decylamine forming an intermediate product;

reacting the intermediate product with corresponding diimine ligands forming final complexes as orange crystals of the [Ir(ppyCH₂NH—C10)₂(bpy-R)]Cl.

Preferably, the iridium(III) chloride salt may be reacted with the 4-(2-pyridyl)benzaldehyde in mixture of 2-ethoxyethanol and H₂O in a ratio of 3:1 (v/v) under reflux for 24 hours in dark in an nitrogen atmosphere. The reductive amination may be conducted with four equivalents of the n-decylamine, followed by the reaction with corresponding diimine ligands in CH₂Cl₂/MeOH (1:1, v/v), giving the final complexes as orange crystals. The following diagram illustrates specific example for synthesizing the dye as described above.

BRIEF DESCRIPTION OF THE DRAWINGS

This patent or application file contains at least one drawing executed in color. Copies of this patent or patent application with color drawing(s) will be provided by the Office upon request and payment of the necessary fee.

Some embodiments of the present invention will now be explained, with reference to the accompanied drawings, in which.

DETAILED DESCRIPTION OF EMBODIMENTS THE INVENTION

The present invention is concerned with a new type of cell membrane staining reagents with novel dye molecules having photo-stable phosphorescent transition metal polypyridine complexes. Experiments were conducted to show that the applications of these complexes as biological imaging reagents were useful for processed mammalian cells.

Studies leading to the present invention have shown that in order for dye molecules to be used effectively as cell membrane staining reagents, the molecules should be able to be attracted to the cell membrane and to remain stable at the cell membrane under different conditions. Otherwise, the dye molecules would be transported away, e.g. within the cells, or are dissociated before detection can be made.

In a broad aspect of the present invention, there is provided a staining dye for staining a biological cell in which the due comprises dye molecules. In order to ensure that the molecules are attracted and adhered to the cell membrane, the molecules are engineered with a positively charged polar head group for attraction to the cell membrane of the cell, and with one or more hydrophobic tail groups for interaction with phospholipids of the cell and for refraining the dye molecule from entering the cytoplasm. In order to address photo-stability of the dye molecules, they are engineered to be transition metal polypyridine complexes having a metal center and ligands. It is to be noted that the complexes are non-organic fluorophores.

Although the present invention encompasses the use of staining dye molecules engineered with any workable transition metal polypyridine complexes having a metal center, experiments show that in specific embodiments phosphorescent complexes of iridium(III), rhenium(I) and ruthenium(II) are suitable and can selectively stain the cell membrane with sufficient stability. Studies have shown that the suitability of these complexes is related to their lipophilicity, formal charges, and molecular sizes. The structural features of these complexes are exemplified by the iridium(III) polypyridine complexes [Ir(N^C-lipid)$_2$(N^N-polar-group)]$^+$.

Studies have shown that such complexes have highly nonpolar lipid moieties, allowing them to interact with the lipid bilayer of the cell membrane, whereas the polar groups will refrain the complexes, and thus the due molecules, from entering the cytoplasm. Thus, the cooperative effects of the lipid and polar group entities will enable the complexes to reside in the cell membrane. Further, the inherent phosphorescence properties of the complexes are exploited for bio-imaging applications. The studies have also shown that phosphorescent iridium(III), rhenium(I) and ruthenium(II) polypyridine complexes can show intense emission upon cellular uptake. It means the use of phosphorescent transition metal polypyridine complexes as cellular staining reagents with an emphasis on cell membrane staining is effective. The use of the transition metal polypyridine complexes as staining dyes of the present invention is to be contrasted with conventional dyes using traditional organic fluorophores. In other words, the present invention makes use of use of phosphorescent transition metal polypyridine complexes as phosphorescent emitters for imaging purposes.

In order to fully appreciate the efficacy of the staining dye of the present invention as described, it is to be understood that conventional dyes using traditional organic fluorophores are disadvantaged in that they suffer from problems of (1) photo-bleaching, (2) self-quenching problems, (3) short-lived fluorescence, and 4) not being utilized for fluorescence-lifetime imaging microscopy (FLIM). To the contrary, the dye molecules of the present invention make use of transition metal polypyridine complexes which fulfil the emission properties. Due to the use of transition metal polypyridine complexes, the complexes are photo-stable and their emission is pH independent. These can allow long-term tracking of cells that have been stained by the complexes. The pH non-independence means the staining can last regardless of change of surrounding cellular environment or experimental conditions. Further, the complexes are phosphorescent in nature, the use of transition metal polypyridine complexes is not limited by problems originating from self-quenching and short emission lifetimes. Yet further, many transition metal polypyridine complexes exhibit environment-sensitive emission, which reflects their local physical (e.g., hydrophobicity and rigidity) and chemical (e.g., pH and pO$_2$) parameters. Their long emission lifetimes also facilitate detection and imaging by FLIM. Furthermore, the involvement of transition metals means that the cellular uptake can be conveniently measured by ICP-MS, which is irrelevant to organic dyes.

Figure 1:
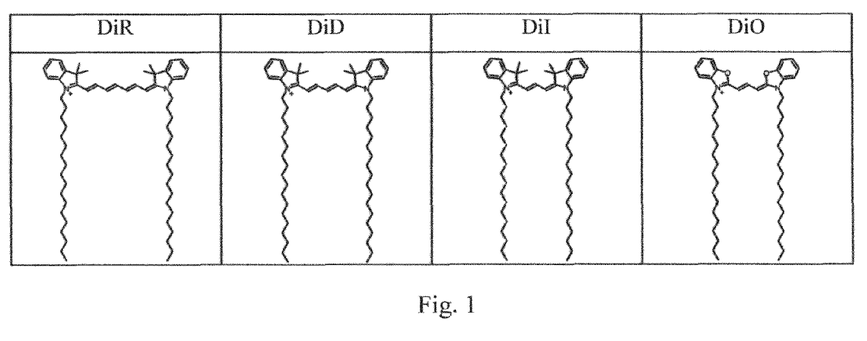
FIG. 1 illustrates the structural formulae of four commercially available cell membrane staining dye molecules.

FIG. 1 illustrates four conventional dye molecules. However, they are deficient in a number of ways. For instance, they are photo-unstable, unable to be attracted to the cell membrane for a long period of time.

Figure 2:
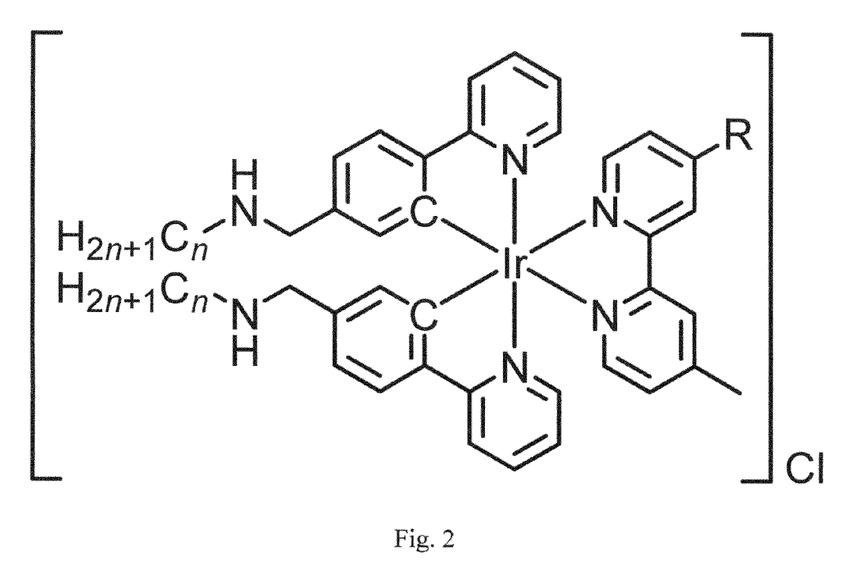
FIG. 2 depicts a general structural formula of an embodiment of a cell membrane staining dye molecule according to of the present invention.
Figure 3:
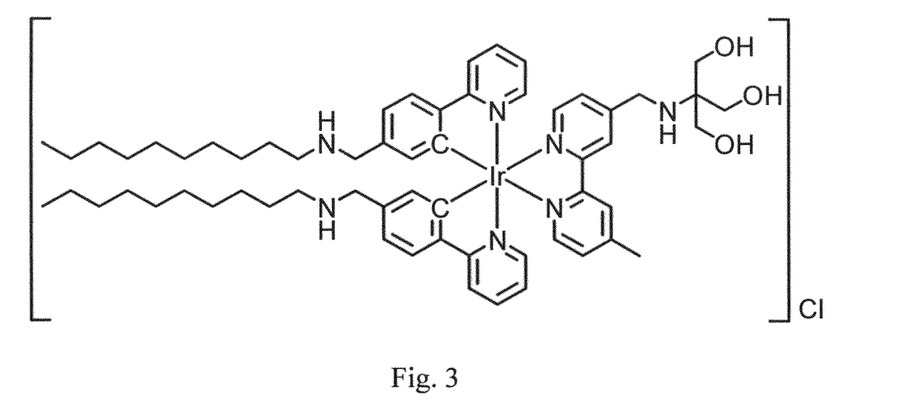
FIG. 3, FIG. 4 and FIG. 5 depict specific structural formulae of three specific embodiments of cell membrane staining dye molecules according to the present invention.
Figure 4:
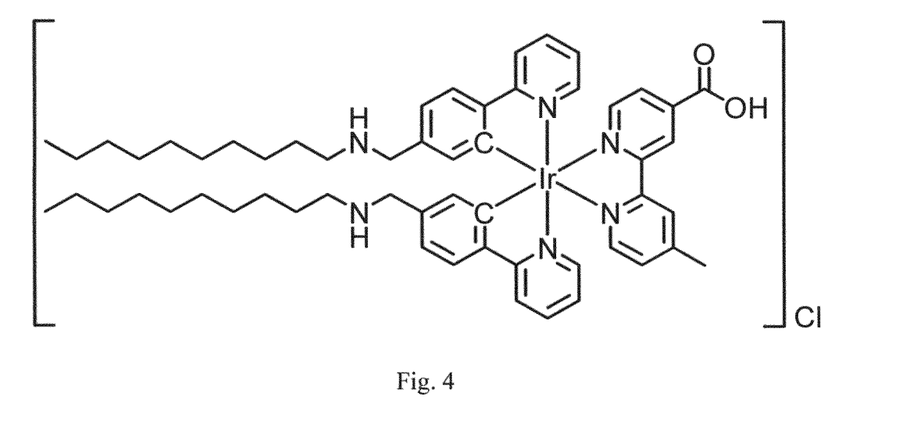
Figure 5:
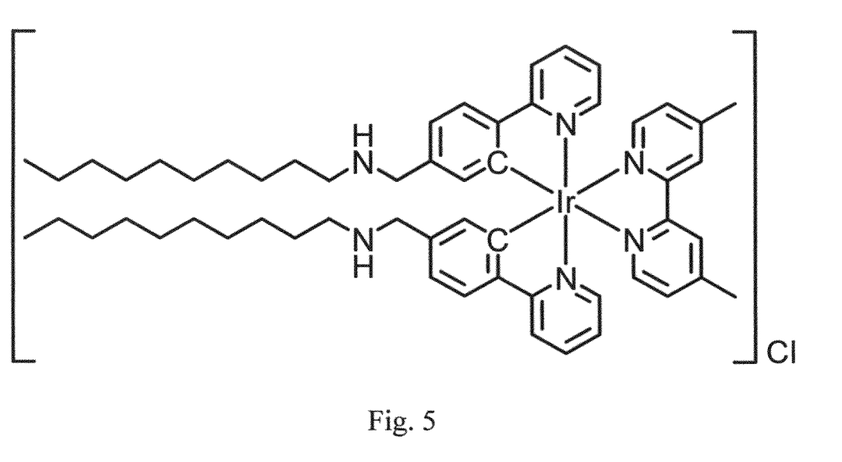

FIG. 2 illustrates a general structural formula of a dye molecule of the present invention. It is shown that it has a relatively large and positively charged polar head group for attraction to cell membrane of the cell. It also has two hydrophobic tails for interaction with phospholipids of the cell membrane and for minimizing the dye molecule entering the cell. FIGS. 3-5 illustrate structural formulae of specific molecules with specifically defined R group.

Figure 6:
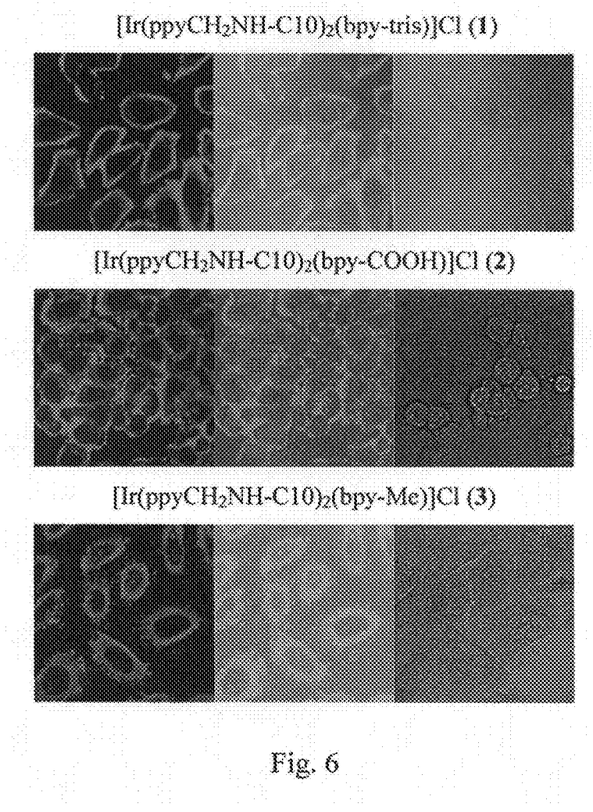
FIG. 6 shows fluorescence laser-scanning confocal microscopy images of HeLa cells treated with complexes (50 µM) at 37° C. for 1 h.
Figure 7:
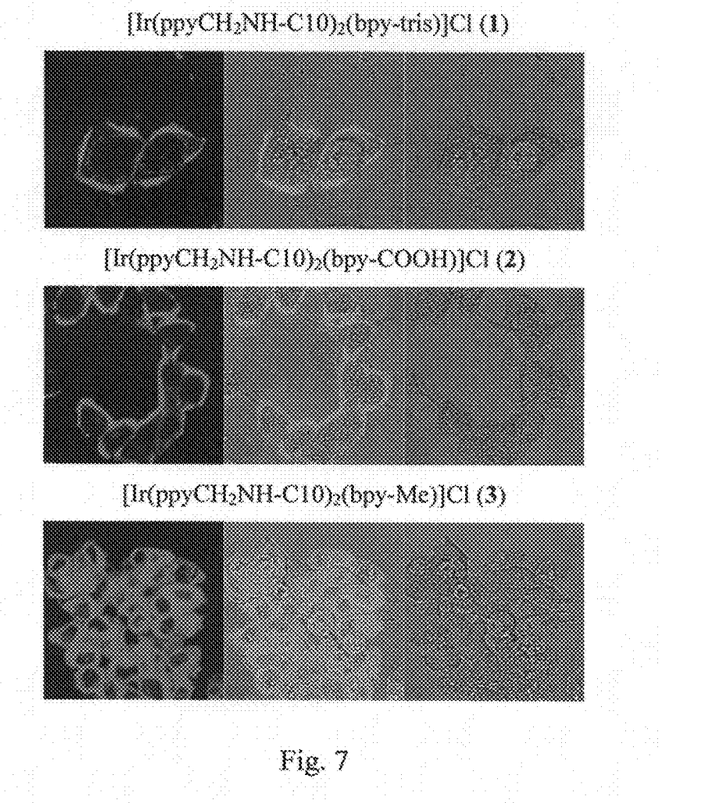
FIG. 7 shows fluorescence laser-scanning confocal microscopy images of MCF-7 cells treated with complexes (50 µM) at 37° C. for 1 h.

Experiments were conducted to show the working of the staining dye of the present invention. HeLa and MCF-7 cells were grown on sterile glass coverslips in a 60-mm tissue culture dish and incubated at 37° C. under a 5% $CO_2$ atmosphere for 48 h. The culture medium was removed and replaced with medium/DMSO (99:1, v/v) containing the complex at a concentration of 50 μM. After incubation for 1 h, the coverslips were washed with PBS (5 mL×3), and then mounted onto slides for measurements. Imaging was performed using a confocal microscope (Leica TCS SPE) with an excitation wavelength at 405 nm. The emission was measured using a long-pass filter at 532 nm. FIG. 6 illustrates experimental results with fluorescence laser-scanning confocal microscopy images of HeLa cells treated with complexes (50 μM) at 37° C. for 1 h. FIG. 7 illustrates experimental results with fluorescence laser-scanning confocal microscopy images of MCF-7 cells treated with complexes (50 μM) at 37° C. for 1 h. The results show that the bpy-tris and bpy-COOH complexes, which have a very polar substituent R on the bipyridine ligand, display much better membrane staining toward HeLa and MCF-7 cells, whereas the bpy-Me complex, with the least polar R among the three complexes, exhibits higher cytoplasmic localization in addition to membrane staining.

Figure 8:
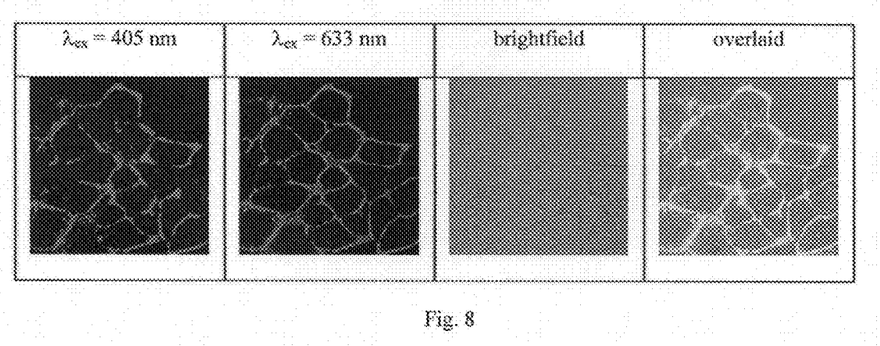
FIG. 8 are fluorescence laser-scanning confocal microscopy images of MCF-7 cells treated with the bpy-tris complex (50 µM, 1 h) and the CellMask™ deep red plasma membrane stain (0.25 µL/ml, 5 min)

Further experiments were conducted to co-stain cells with the complex [Ir(ppyCH$_2$NH—C10)$_2$(bpy-tris)]Cl and the CellMask™ deep red plasma membrane stain. It is found that there is a high degree of colocalization (colocalization coefficient=92.9%). Please see FIG. 8 showing fluorescence laser-scanning confocal microscopy images of MCF-7 cells treated with the bpy-tris complex (50 μM, 1 h) and the CellMask™ deep red plasma membrane stain (0.25 μL/ml, 5 min).

In general, phosphorescent transition metal polypyridine complexes should have the following technical advantages.
(1) The transition metal complexes are photostable.
(2) The use of transition metal complexes is not limited by problems originating from self-quenching.
(3) Their long emission lifetimes facilitate time-resolved detection and imaging.
(4) The cellular uptake can be conveniently measured by ICP-MS, which is irrelevant to organic dyes.

Figure 9:
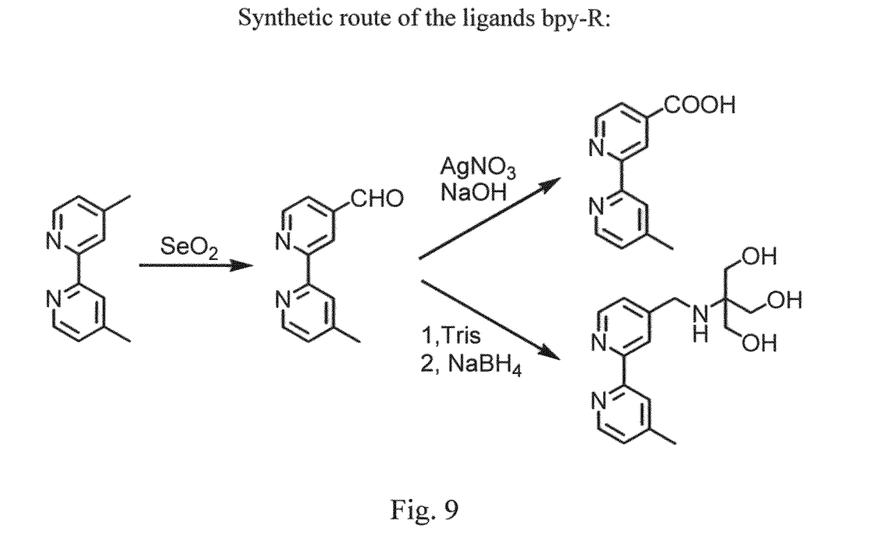
FIG. 9 illustrates a route for synthesis of the ligands bpy-R in the complexes of staining dye molecules according to the present invention.

FIG. 9 depicts, by way of example, the route for synthesis of ligands bpy-R of staining dye of the present invention. 4,4'-Dimethyl-2,2'-bipyridine was oxidized to 4-aldehyde-4'-methyl-2,2'-bipyridine by selenium oxide. Further oxidation of the aldehyde compound by Ag$_2$O (generated in situ by reaction of silver nitrate and sodium hydroxide) gave 4-carboxy-4'-methyl-2,2'-bipyridine (bpy-COOH) as white powder. Reductive amination of the aldehyde compound with tris(hydroxymethyl)aminomethane in the presence NaBH$_4$ yielded the bpy-tris ligand.

Figure 10:
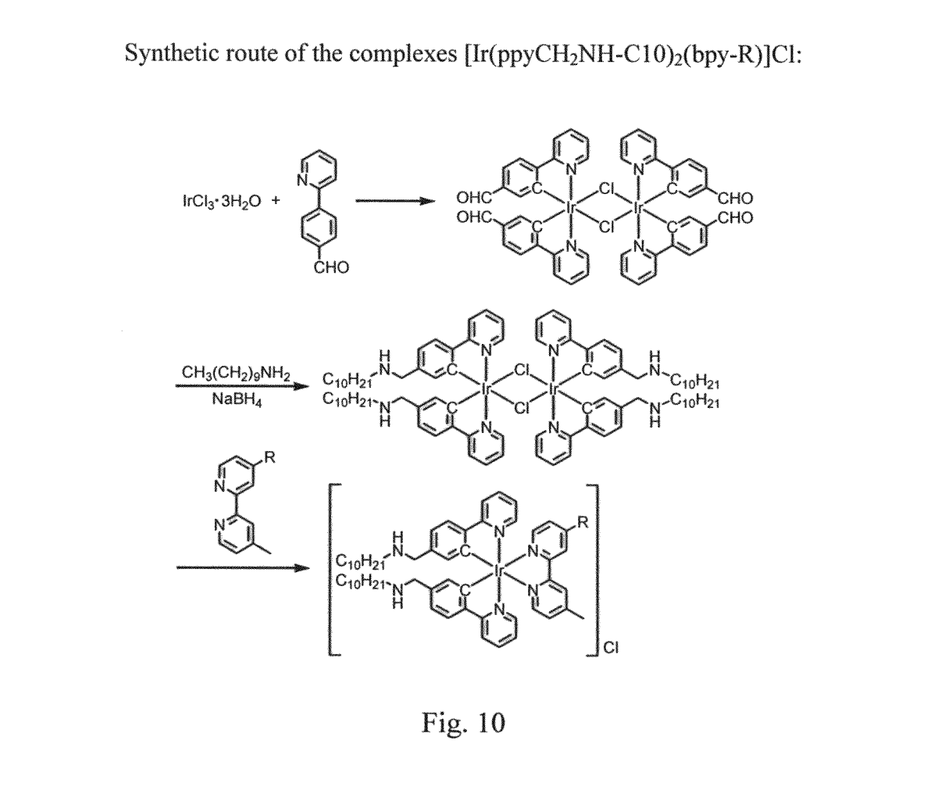
FIG. 10 illustrates a route for synthesis of the complexes [Ir(ppyCH$_2$NH—C10)$_2$(bpy-R)]Cl of staining dye molecules according to the present invention.

FIG. 10 depicts, by way of example, the route for synthesis of complexes of staining dye of the present invention. In an exemplary procedure, the iridium(III) chloride salt was reacted with 4-(2-pyridyl)benzaldehyde in 2-ethoxyethanol/H$_2$O (3:1, v/v) under reflux for 24 h in the dark in an nitrogen atmosphere. The orange dimer was collected by centrifugation, washed with ethanol/H$_2$O (95:5 v/v), and air dried. Reductive amination with four equivalents of n-decylamine was performed, followed by the reaction with corresponding diimine ligands in CH$_2$Cl$_2$/MeOH (1:1, v/v), giving the final complexes as orange crystals.

It should be understood that certain features of the invention, which are, for clarity, described in the content of separate embodiments, may be provided in combination in a single embodiment. Conversely, various features of the invention which are, for brevity, described in the content of a single embodiment, may be provided separately or in any appropriate sub-combinations. It is to be noted that certain features of the embodiments are illustrated by way of non-limiting examples. Also, a skilled person in the art will be aware of the prior art which is not explained in the above for brevity purpose.

The invention claimed is:

1. A staining dye for staining a biological cell, comprising dye molecules with a positively charged polar head group for attraction to cell membrane of the cell, and one or more hydrophobic groups for interaction with phospholipids of the cell membrane and for minimizing the dye molecules from entering the cell, wherein the dye molecules are transition metal polypyridine complexes having a metal center and ligands which are non-organic fluorophores.

2. A dye as claimed in claim 1, wherein the hydrophobic group has one or more hydrophobic tails.

3. A dye as claimed in claim 1, wherein the complexes have non-polar moieties for interaction with lipid bilayer of the cell membrane and polar groups for refraining the complexes from entering the cytoplasm.

4. A dye as claimed in claim 1, wherein the metal center is selected from a group containing iridium(III), rhenium(I) and ruthenium(II).

5. A dye as claimed in claim 1, wherein the chemical formula and the structural formula of the dye molecules are:

respectively, wherein n≥4; R is COOH or tris (CH$_2$NHC(CH$_2$OH)$_3$.

* * * * *